United States Patent
Zantl et al.

(10) Patent No.: US 9,915,593 B2
(45) Date of Patent: Mar. 13, 2018

(54) METHOD OF POSITIONING AN ORGANIC, BIOLOGICAL AND/OR MEDICAL SPECIMEN

(75) Inventors: Roman Zantl, Baldham (DE); Elias Horn, München (DE)

(73) Assignee: IBIDI GMBH, Martinsried (DE)

( * ) Notice: Subject to any disclaimer, the term of this patent is extended or adjusted under 35 U.S.C. 154(b) by 452 days.

(21) Appl. No.: 12/777,558

(22) Filed: May 11, 2010

(65) Prior Publication Data

US 2010/0291613 A1 Nov. 18, 2010

(30) Foreign Application Priority Data

May 13, 2009 (EP) .................................... 09006487

(51) Int. Cl.
*G01N 1/36* (2006.01)

(52) U.S. Cl.
CPC ..................... *G01N 1/36* (2013.01)

(58) Field of Classification Search
None
See application file for complete search history.

(56) References Cited

U.S. PATENT DOCUMENTS

| | | | |
|---|---|---|---|
| 4,689,307 A | 8/1987 | Schwartz | |
| 5,720,928 A * | 2/1998 | Schwartz | C12Q 1/683 422/129 |
| 5,939,251 A | 8/1999 | Hu | |
| 2003/0036067 A1* | 2/2003 | Schwartz | C12Q 1/68 435/6.12 |
| 2006/0099114 A1* | 5/2006 | Caldwell et al. | 422/99 |
| 2008/0020455 A1 | 1/2008 | Zantl et al. | |

FOREIGN PATENT DOCUMENTS

| | | |
|---|---|---|
| DE | 102004041941 A1 | 3/2006 |
| EP | 1880764 A1 | 1/2008 |
| WO | 2005103685 A1 | 11/2005 |

OTHER PUBLICATIONS

Invitrogen Catalog 2001, Invitrogen, Carlsbad, CA, 2001, pp. 278-280 and 284-286.*

* cited by examiner

*Primary Examiner* — James Martinell
(74) *Attorney, Agent, or Firm* — Moore & Van Allen PLLC; Henry B. Ward, III

(57) ABSTRACT

The invention relates to a method of positioning an organic, biological and/or medical specimen in a desired partial region of a specimen carrier, comprising the steps arrangement of a gel in a partial region of the specimen carrier, polymerization or gelification of the gel, by means of which a polymerized gel is obtained, whereby the polymerized gel at least partially, in particular horizontally, delimits the desired partial region and introduction of the specimen into the specimen carrier, in particular into the desired partial region of the specimen carrier.

23 Claims, 24 Drawing Sheets

METHOD OF POSITIONING AN ORGANIC, BIOLOGICAL AND/OR MEDICAL SPECIMEN

FIELD OF THE INVENTION

The invention relates to a method of positioning an organic, biological and/or medical specimen in a desired partial region of a specimen carrier. In particular the invention relates to a method of positioning a specimen with the aid of a gel.

BACKGROUND OF THE INVENTION

In particular specimen carriers are used in the fields of cell biology and medicine for the examination of organic, biological and/or medical specimens. In certain experiments it is of advantage to arrange the specimens only in a part of the volume of the specimen carrier, whereby other regions of the volume are to remain free.

For example, a predetermined, for example high, specimen density can be required for carrying out an experiment in a certain volume region, perhaps during the simulation of solid tumour tissue. Similarly, an experiment is conceivable in which different types of specimen are introduced into a predetermined volume of the specimen carrier separated from one another in order, for example, to observe their mutual interference.

Often however, when filling a specimen carrier a random arrangement of the specimens occurs.

BRIEF SUMMARY OF THE INVENTION

Therefore, the object of the invention is to provide a method of positioning an organic, biological and/or medical specimen, which facilitates the specimen to be positioned in a desired partial region of the specimen carrier.

This object is solved by a method according to Claim 1.

The process according to the invention of positioning an organic, biological and/or medical specimen in a desired partial region of a specimen carrier comprises the steps:
arrangement of a gel in a partial region of the specimen carrier,
polymerisation or gelification of the gel, by means of which a polymerised gel is obtained, whereby the polymerised gel delimits at least partially, in particular horizontally, the desired partial region, and
introduction of the specimen into the specimen carrier, in particular into the desired partial region of the specimen carrier.

A defined spatial positioning of the specimen can be achieved through the use of a polymerised gel for the delimitation of a desired partial region, in particular a desired partial volume, into which the specimen is positioned.

The organic, biological and/or medical specimen can be a biological cell. In particular the method can be carried out for a plurality of cells. In this way a desired cell distribution and/or cell density in a desired partial region of the specimen carrier can be achieved. In addition the specimen can be a micro-organism or DNA.

A viscoelastic fluid is designated as a gel. The fluid properties of a gel can be between those of an ideal liquid and those of an ideal solid. A gel can form a three-dimensional spatially stable matrix. Generally, a gel can assume a gel form through cross-linking with cross-linkers and/or by the undercutting of a temperature. The first case can be designated as polymerisation and the second as gelification.

The gel can comprise a solid and a liquid phase and can, in particular, be a colloid. The gel can comprise gel particles, whereby the gel particles change the spatial extent, in particular by enlargement, during the polymerisation or gelification.

The gel can comprise or correspond to Collagen 1 gel, matrigel, polyacrylamide, agarose, hyaluronic acid and/or superabsorbent materials, such as for example, polyacrylic acid.

The gel can be formed such that a specimen is fixed or freely movable in the gel.

Polymerisation or gelification can comprise an introduction of liquid and/or cross-linkers into the specimen carrier, in particular into the gel.

The specimen carrier can comprise at least one region for the arrangement of a specimen. In particular the region can be a three-dimensional spatial region or a three-dimensional volume. The region can comprise a partial region, in particular a desired partial region, in particular whereby the partial region or desired partial region is a three-dimensional spatial region or a three-dimensional volume. The partial region or desired partial region can be smaller in at least one, in particular horizontal, direction than the region itself. The partial region or desired partial region can be smaller in all directions than the region itself. The partial region or desired partial region can be without delimitation due to the specimen carrier in at least one, in particular horizontal, direction. In other words further partial regions can border the partial region or desired partial region.

The specimen carrier can comprise a plastic, in particular COC (cyclo-olefin copolymer), COP (cyclo-olefin polymer), PS (polystyrene), PC (polycarbonate) or PMMA (polymethylmetacrylate). The specimen carrier can be formed as an injection moulded part. The specimen carrier can comprise a bottom plate, in particular whereby the specimen carrier lies on the bottom plate in operation, and whereby the bottom plate can comprise a plastic and or glass. The bottom plate can be thin, for example between 1 µm and 300 µm. In this way high resolution microscopy through the bottom plate can be facilitated.

The specimen carrier can comprise a cover plate, whereby the cover plate is joined, in particular directly, to the bottom plate in a manner sealed to fluids.

The specimen carrier, bottom plate and/or cover plate can have a predetermined intrinsic fluorescence, which is lower than or equal to the intrinsic fluorescence of COC or COP or a conventional cover slip, and/or a predetermined refractive index, in particular >1.2 and/or <1.7. In particular the intrinsic fluorescence can be lower than or equal to the intrinsic fluorescence of a conventional cover slip (for example pure white glass in the hydrolytic class 1 (such as Menzel cover slips, in particular with the thickness no. 1.5)). The predetermined refractive index can in particular be >1.2 and/or <1.7. With a high quality material of this nature microscopic examinations can be carried out in an advantageous way. For example, the double refraction can be so low that DIC (Differential Interference Contrast) is possible. A low intrinsic fluorescence facilitates carrying out fluorescence measurements.

In particular the bottom plate and/or cover plate can have an anti-reflection coating for the frequency range of electromagnetic radiation used in microscopy. In this way the transmission through the bottom plate and/or cover plate can be increased so that single-molecule measurements are possible with the aid of fluorescence.

The specimen carrier can comprise a cavity for the accommodation of a specimen. At least one opening can lead to the cavity for filling the cavity with the specimen and/or a liquid or emptying it of same. The cavity can be formed by recesses in the cover plate and/or in the bottom plate.

The specimen carrier can be dimensioned such that the volume of the cavity lies in the region of 5 µl to 1000 µl, in particular between 100 µl and 500 µl. Thus, the specimen carrier can be used for micro-fluidic examinations.

In particular the specimen carrier can comprise a bottom plate and a cover plate, whereby the cover plate and/or the bottom plate have recesses and are joined together in a manner sealed to fluids so that the recesses form at least two reservoirs and a channel which connects the reservoirs. Each of the reservoirs can be filled through an opening through the cover plate or bottom plate and the cross-sectional area of the channel at the outlet of the channel opening into one of the reservoirs can at least be 5 times, in particular at least 20 times smaller than the maximum cross-sectional area of the reservoir in parallel to this cross-sectional area of the channel. The channel can be filled via at least one opening, in particular whereby the at least one opening corresponds to an outlet of a filling channel.

The polymerised gel can be arranged and/or formed such that, in particular during the introduction of the specimen into the specimen carrier, dissemination of the specimen out of the desired partial region within the specimen carrier, in particular in the horizontal direction, is prevented. In this way positioning of the specimen in the desired partial region can be achieved.

In particular, the polymerised gel can be formed such that the specimen cannot penetrate into the polymerised gel. Alternatively or additionally, the polymerised gel can be arranged such that emission of the specimen out of the desired partial region, in particular into other partial regions of the specimen carrier, is prevented.

In the desired partial region no polymerised gel can be arranged or polymerised gel can be arranged in the desired partial region, in particular in the whole of the desired partial region. In particular, gel can be arranged or not arranged in the desired partial region, in particular in the whole of the desired partial region, after the step of polymerisation or gelification.

If after the step of polymerisation or gelification no polymerised gel is arranged in the desired partial region, at least one boundary area or external area of the desired partial region can comprise the polymerised gel and in this way emission of the specimen out of the desired partial region, in particular into another partial region of the specimen carrier, can be prevented.

If after the step of polymerisation or gelification polymerised gel is arranged in the desired partial region, in particular in the whole of the desired partial region, the specimen can be arranged in the polymerised gel and thus emission of the specimen within the specimen carrier prevented. In other words the partial region of the specimen carrier, in which the polymerised gel is arranged, can correspond to the desired partial region.

In particular the introduction of the specimen can comprise an introduction of the specimen into the gel, in particular whereby the introduction of the specimen into the gel occurs before the arrangement of the gel. In this case the specimen can be introduced into the specimen carrier with the gel and/or arranged with the gel in a partial region of the specimen carrier. In this case the partial region of the specimen carrier, in which the polymerised gel is arranged, corresponds to the desired partial region. In particular in this case a three-dimensional or spatial arrangement of the specimen can be achieved.

The polymerisation or gelification of the gel can occur before, during and/or after the arrangement of the gel. In particular the arrangement of the gel can comprise an introduction of the gel into the specimen carrier or correspond to an introduction of the gel into the specimen carrier.

The polymerisation or gelification of the gel can at least partially occur in a casting mould, in particular before the introduction and/or arrangement of the gel in the specimen carrier. In this way the polymerised gel can be provided in a predetermined shape and introduced and/or arranged in a partial region of the specimen carrier in the predetermined shape.

Each of the above described methods can also comprise introduction of a further gel into the specimen carrier, in particular into the desired partial region of the specimen carrier. In this case the gel can be designated as the first gel and the further gel as the second gel.

The further gel can exhibit one or a plurality of features of the gel described above. The further gel can be arranged in a partial region which borders the desired partial region. In particular the further gel can be penetrable or impenetrable for the specimen.

Alternatively or additionally, the further gel can be introduced into the desired partial region, in particular after the polymerisation or gelification of the first gel.

In particular the specimen can be introduced into the specimen carrier with the further gel, in particular in the form of a suspension in the further gel. In this way a three-dimensional or spatial arrangement of the specimen can be achieved.

A specimen can be introduced into the gel and an identical and/or different specimen can be introduced into the further gel. In this way the mutual interference of specimens can be examined.

The introduction of the further gel can comprise an arrangement of the further gel in a partial region of the specimen carrier, in particular in the desired partial region of the specimen carrier.

A chemical substance, in particular a chemoattractant can be introduced into the gel and/or the further gel. In this way the method for producing diffusively structured gradients can be used.

The arrangement of the gel can comprise an arrangement of a positioning element in a partial region of the specimen carrier, in particular whereby the partial region comprises the desired partial region, and whereby the positioning element prevents a dissemination of the gel into the desired partial region or out of the desired partial region. In other words the partial region of the specimen carrier in which the gel is arranged can be partially or completely delimited or left free by means of the positioning element.

The arrangement of the gel and/or the introduction of the further gel can comprise an arrangement and/or introduction of the gel and/or of the further gel into the positioning element, in particular into a partial region of the positioning element. In particular the arrangement of the gel and/or of the further gel can comprise an arrangement of the positioning element in the specimen carrier, in particular whereby the arrangement of the positioning element occurs after the introduction of the gel and/or of the further gel into the positioning element, in particular into a partial region of the positioning element.

The arrangement of the positioning element in the specimen carrier can be preceded by an introduction of the positioning element into the specimen carrier. The positioning element can be arranged in a channel of the specimen carrier, in particular whereby the channel connects two reservoirs. The channel can be sealed off from the positioning element, in particular with a silicone oil and/or with an O-ring seal.

The positioning element can comprise one or a plurality of through holes, in particular such that when the positioning element is joined to the specimen carrier, in particular to a surface of the specimen carrier, at least one blind hole is produced. The desired partial region can correspond to at least one blind hole. The desired partial region can correspond to the through hole or comprise the through hole.

The desired partial region can comprise the surface region of the specimen carrier covered by the positioning element. In particular a boundary area of the desired partial region can correspond to the surface region of the specimen carrier covered by the positioning element.

The material of the positioning element can be frozen water, a polymer which, in particular, can be depolymerised by UV radiation, a metal and/or a plastic.

A surface of the positioning element can be formed such that the positioning element can be reversibly joined to a surface of the specimen carrier. In particular a surface of the positioning element can be formed such that the positioning element can be removed non-destructively and/or free of residue from the surface of the specimen carrier. In this way the positioning element can be removed from the specimen carrier after the arrangement of the gel, in particular after the polymerisation or gelification of the gel, without the surface of the specimen carrier being damaged.

The positioning element can be removed during or after the polymerisation or gelification of the gel. The positioning element can be removed before, during or after the introduction of the specimen. In particular the specimen can be introduced and/or arranged with the gel, whereby a positioning element delimits the desired partial region such that an emission of the gel and the specimen out of the desired partial region is prevented. Thereafter the gel can be polymerised or gelified and then the positioning element removed.

The desired partial region can be fully delimited by the polymerised gel or by the polymerised gel and the specimen carrier. In other words the desired partial region can correspond to a cavity, whereby the cavity is formed by the specimen carrier and/or the polymerised gel. The cavity can comprise an opening, so that the cavity can be filled with a specimen, gel and/or liquid or correspondingly emptied. The opening can in particular correspond to the outlet of a filling channel.

The gel particles of the gel, in particular of the unpolymerised gel, can be formed such that it cannot encroach into the desired partial region. In particular when the desired partial region corresponds to a cavity, the gel particles can have a mean diameter and/or a mean minimum spatial extent which are larger than the maximum spatial extents or longitudinal extent of the cavity at the boundary area to the partial region in which the gel is arranged.

The specimen carrier can comprise a cavity whereby the desired partial region is arranged in the cavity. In other words the desired partial region can correspond to a partial region of a cavity. In particular the specimen carrier can comprise two reservoirs and a channel, which connects the reservoirs, whereby the desired partial region corresponds to the channel or the channel comprises the desired partial region.

The partial region of the specimen carrier in which the gel is arranged can correspond to a partial region of the cavity, in particular a reservoir. The volume of the partial region or reservoir can be smaller, in particular 5%-10% smaller, than the volume of the polymerised or gelified gel. Due to the fact that the gel cannot completely swell up due to the small size of the volume of the partial region or reservoir, an osmotic pressure can arise in the gel in the partial region or reservoir, and an emission of the specimen out of the desired partial region, in particular out of the channel into the reservoir, can be prevented.

The cavity, in particular the dimensions of the cavity, can be formed such that the gel is held in the desired partial region, in particular in the channel, by capillary forces.

The polymerised gel can vertically delimit the desired partial region, in particular on its upper side and/or underside. In particular the polymerised gel can correspond to a boundary layer between the specimen and a surface of the specimen carrier. The boundary layer can have a constant thickness, in particular between 1 µm and 40 µm.

The invention also provides a use of a gel for positioning an organic, biological and/or medical specimen in a desired partial region of a specimen carrier, whereby the gel is arranged in a partial region of the specimen carrier, polymerised or gelified, by means of which a polymerised gel is obtained, whereby the polymerised gel delimits the desired partial region at least partially, in particular horizontally, and the specimen is introduced into the specimen carrier, in particular into the desired partial region of the specimen carrier.

The use of the gel can exhibit one or a plurality of the features described in the method described above.

The invention also provides a use of a gel for introduction into a specimen carrier, whereby the gel is polymerised or gelified and whereby the polymerised or gelified gel prevents adhesion of an organic, biological and/or medical specimen on a surface of the specimen carrier. In this way durotaxis of living cells can be prevented.

The specimen can be arranged in a further gel. In other words the polymerised gel can correspond to an intermediate layer between a further gel with the specimen in suspension and a surface of the specimen carrier. The intermediate layer can have a constant thickness, in particular between 1 µm and 40 µm.

The gel, the further gel and/or the specimen carrier can exhibit one or a plurality of the features described above. In particular the gel and the further gel can comprise the same material.

The invention also provides a specimen carrier, in particular for use in one of the methods described above, comprising a gel in a partial region of the specimen carrier.

The gel and/or the specimen carrier can exhibit one or a plurality of the features described above.

In particular the specimen carrier can comprise two reservoirs and a channel which connects the reservoirs, whereby gel can be arranged in at least one reservoir, so that when the gel is polymerised or gelified, the polymerised or gelified gel completely fills the at least one reservoir.

The gel, in particular the gel particles of the gel, can be formed such that they cannot encroach into the channel from the at least one reservoir.

The specimen carrier can be used as a micro-fluid device for producing diffusively structured gradients.

The invention also provides a positioning element, in particular for use in one of the methods described above, whereby the positioning element is formed such that an emission of the gel into a desired partial region or out of a desired partial region is prevented.

In particular the positioning element can exhibit one or a plurality of the features described above. In particular the positioning element can have a through hole and/or a recess.

The positioning element can comprise a plastic, in particular COC (cyclo-olefin copolymer), COP (cyclo-olefin polymer), PS (polystyrene), PC (polycarbonate) or PMMA (polymethylmetacrylate). The positioning element can be formed as an injection moulded part, in particular as a single injection moulded part. Alternatively or additionally, the positioning element can comprise a bottom plate and a cover plate, whereby the bottom plate and/or the cover plate have a recess, in particular so that when the bottom plate is connected, in particular in a manner sealed to fluids and/or directly, to the cover plate, a through hole and/or a blind hole is formed in the positioning element.

The positioning element can be dimensioned such that it can be introduced and/or arranged in a cavity, in particular in a channel, of a specimen carrier, in particular of a specimen carrier described above.

The specimen carrier can comprise two reservoirs and a channel connecting the reservoirs. In this case a through hole in the positioning element can have a cross-section, which corresponds to a cross-section of the channel perpendicular to the joining line of the two reservoirs. The through hole can in this case run parallel to the joining line of the two reservoirs in the positioning element when the positioning element is arranged in the specimen carrier.

BRIEF DESCRIPTION OF THE DRAWINGS

Further features and advantages are explained in the following based on exemplary figures. The following are illustrated.

DETAILED DESCRIPTION OF THE INVENTION

Figure 1:
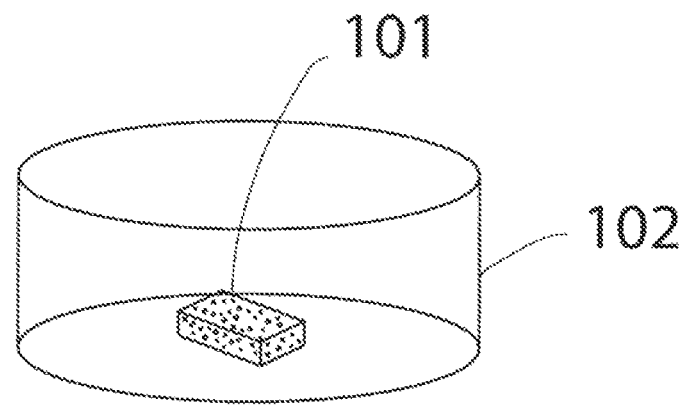
FIG. 1 an example of a specimen carrier and a gel arranged in it.

A partial region of a volume of a specimen carrier can be filled with polymerised gel, and in fact such that other partial regions can be filled retrospectively with liquids or gels. For example the gel can be first arranged in the liquid, i.e. in the non-polymerised or non-gelified form, in a partial region of the specimen carrier and then allowed to polymerise or gelify. One or a plurality of initially dry or only slightly moistened pieces of gel can be introduced into the partial region, whereby due to their size they cannot encroach into one or a plurality of bordering partial regions. Alternatively, a positioning element, for example a removable barrier, can be used which can be removed after polymerisation. Frozen water which is allowed to melt, a polymer which can be depolymnerised, for example by UV radiation, or also a slide of, for example, plastic or metal can be used as positioning element.

Alternatively or additionally, a gelatine, which has swollen to 80%, 90% or 100% of its maximum expandable size, can be introduced into a casting mould where it cools down, whereby the casting mould is formed such that recesses or indentations arise in the gelified gel. If the piece of gel is then introduced into a partial region of the specimen carrier in which the piece of gel is arranged, but the recesses or indentations are not filled in, small volumes, like channels for example, are produced, which can then be filled with a liquid, e.g. a non-polymerised gel. In other words the desired partial region can be formed by recesses or indentations in the polymerised or gelified gel.

A further alternative is to fill a partial region with gel and to allow it to polymerise or gelify and to fill the bordering region with a second liquid or non-polymerised or non-gelified gel.

In the following it is assumed that the organic, biological and/or medical specimen involves one or a plurality of biological cells. It is self-evident that the method according to the invention is not restricted to this and that also any other organic, biological and/or medical specimens are possible.

To culture cells in gels the cells are suspended in a non-polymerised gel, such as for example Collagen 1 gel, which can be obtained from rats' tails or from cattle. Other gels are, for example, matrigel, polyacrylamide, agarose or also hyaluronic acid, which, with so-called cross-linkers, can be made to produce a three-dimensional spatially stable matrix. A further group of strongly swelling gels are the so-called superabsorbent materials such as for example, polyacrylic acid. Superabsorbent materials can absorb more than one hundred times their own weight of aqueous liquid, whereby the actual absorbing capability depends in part on the salt content of the liquid.

With migration assays with cells, collagen gel and/or matrigel can be used, because these gels, obtained from biological organisms, can be split by the cell's own enzymes, so that cells can find a way through the gels. This is in particular necessary, because the mesh size of many gels with approx. 100 nm is significantly smaller than the cell diameter (approx. 3-20 μm). If, for example, there is a requirement to fix cells at a certain point to observe them microscopically over longer time periods, it is advantageous to use gels for which cells generally possess no break-up enzymes, such as for example, polyacrylamide, agarose or three-dimensionally cross-linked hyaluronic acid. The cells also cannot normally migrate into these gels.

Generally, a differentiation can be made between gels which assume a gel form through cross-linking with cross-linkers and gels which, for example, gelify by the undercutting of a temperature. In the following the first case is designated as polymerisation and the second as gelification.

The gels can differ from one another by the stability of shape in the gel-type phase. Agarose and gelatine gels are, for example, firm and retain their form appropriately. The stability of shape of Collagen 1 gels depends on the concentration of the Collagen 1 in the medium. Generally, they do not exhibit the strength of, for example, agarose or gelatine.

In certain experiments it is advantageous to introduce the cells only in one part of the volume of the specimen carrier, whereby other regions should not be occupied by cells. For example it may be that a certain, for example high, cell density is required, such as for the simulation of solid tumour tissue, for conducting an experiment in a certain volume region. If the complete available volume of the specimen carrier were filled with gel with an appropriately high cell density, the cells may be insufficiently supplied with nutrients and thus rendered unusable for biological experiments.

Similarly, an experiment is conceivable in which there is a requirement to introduce different types of cells separately into a gel-type volume, for example to observe the effect of the respective other cell culture on the cell migration. A further application example is that of small spheres, which, for example, are to be filled with a chemoattractant. These are, for example, to be suspended in a narrow channel in a Collagen 1 gel, Cells in Collagen 1 gel are also to be introduced around this narrow channel to analyse whether the cells move in the direction of the chemoattractant, which is gradually discharged from the small spheres, which act as point-shaped sources.

A further example is the observation of the chemotaxis of, for example, suspension cells in three dimensions. To do this, cells which are suspended in a three-dimensional gel are introduced into an observation region. Two large reservoirs can border the region in opposite directions, whereby both reservoirs contain the same medium, which has a low nutrient content, and in one of the two reservoirs, for example, a chemoattractant is released in a suitable concentration. In this way a diffusively structured gradient is produced over the observation region. In order to be able to observe the cell migration and to be able to microscopize the diffusive gradient over sufficiently long time periods, the observation region is designed such that it joins the two reservoirs with only a small cross-section and exhibits only a low height. In this way the transport of substances through diffusion is slowed down. If low resolution object lenses are used, e.g. 4×, the depth of focus is sufficient to determine the lateral, two-dimensional positions parallel to the focus plane of cells within the observation region using a single digital exposure. Alternatively, picture stacks can also be taken and combined by means of image analysis or, for example, confocal exposures made, or work carried out with the aid of 3D holographic microscopy to track the co-ordinates of the cells over time in three dimensions.

If cells are introduced into gels in very flat channels, the problem can occur in that the cells settle on the bottom of the specimen carrier because of their higher density. The bottom is typically made of glass or plastic. Once the cells are in contact with the bottom, adherent cells, for example endothelial cells such as HUVEC or many tumour cell lines such as HeLa or HT1080, fix themselves to the hard surface. This is known as durotaxis. If the cell behaviour is to be observed in three dimensions, i.e. in a soft gel, durotaxis is a disturbing effect, because the cells adhering to the surfaces generally exhibit the same behaviour as in a conventional, two-dimensional cell culture, e.g. on a plastic Petri dish surface.

In this case one solution is to coat the hard surface with a gel which is impenetrable by cells, whereby the gel layer should have a thickness of at least 1 μm to 40 μm in order to be discerned as soft by the cells. Thinner layers can have an effect on cells which is as hard as the coated surface itself. If the gel layer is coated over with a further gel, which is penetrable to cells and in which cells are suspended during the filling process, the cells which settle on the bottom cannot through durotaxis adhere to the surface of the lower gel layer of a different type. After the polymerisation or gelification of the further gel the cells can be observed in the three-dimensional gel.

Alternatively, it can be advantageous in certain cases when the lower gel layer consists of the same gel as the further gel which is to be coated later and which contains the cell suspension. Settling cells do not in this way come into contact with another gel, which could have a disturbing effect. On the other hand, also in this configuration, the cells cannot fall to the bottom and adhere to the hard container surface.

The durotaxis is also a disturbing effect in the case where cells are to be cultured in a very small volume. Spherical tumour cells with a diameter of approx. 10 to 20 μm, which are suspended in a gel, can form thin, tubular membrane protuberances (nanotubes), which can be many micrometers long. If cells of this nature are to be observed in three dimensions, the nanotubes detect a hard surface even if the cells are not touching the hard surface (at least as far as can be judged with a conventional optical microscope).

FIG. 1 illustrates a gel 101, for example of Collagen 1, which is loaded with cells, and which is arranged in a Petri dish 102. In particular the gel 101 is arranged in a desired partial region of the Petri dish 102. In this case the desired partial region is completely filled with, in particular, polymerised gel. The polymerised gel can prevent spreading of the specimen within the Petri dish 102. The cells can be arranged three-dimensionally in the gel.

Figure 2:
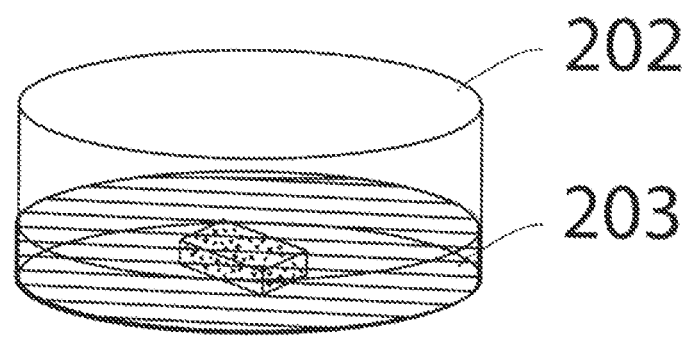
FIG. 2 an example of a specimen carrier and a first and second gel arranged in it.

FIG. 2 illustrates a gel loaded with cells in a desired partial region of the Petri dish 202, whereby a partial region bordering the desired partial region is filled with a further gel 203. The further gel 203 can be a non-polymerised or a polymerised Collagen 1 gel and contain no specimen. In this way a small gel region with cells is produced in a large gel volume. Alternatively, for the further gel 203 a gel could also be used into which the cells could not migrate, e.g. agarose or polyacrylamide, to keep the cells held trapped in the desired partial region.

Figure 3:
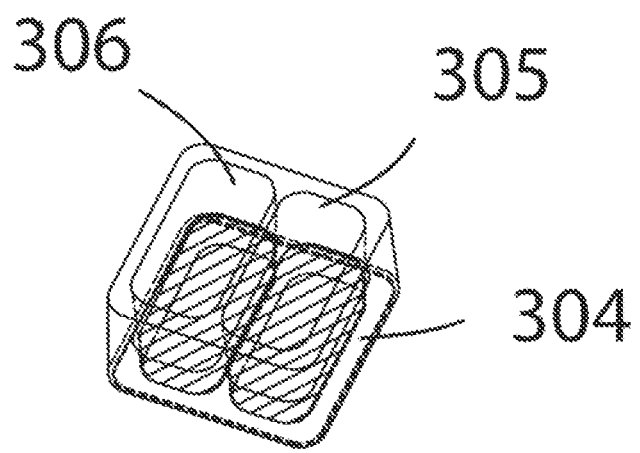
FIG. 3 an example of a positioning element.

FIG. 3 illustrates an example of a positioning element 304. It corresponds to a "Culture Insert" from the company ibidi GmbH. With the aid of the positioning element 304 two cell growth areas or growth volumes can be produced separated from one another. If the positioning element with the through holes 305 and 306 is connected to a surface of a specimen carrier, partial regions can be produced which can be filled with cell suspensions and/or gels in which cells are suspended. Alternatively, a gel without cells can also be used. These partial regions can correspond to blind holes.

Figure 4:
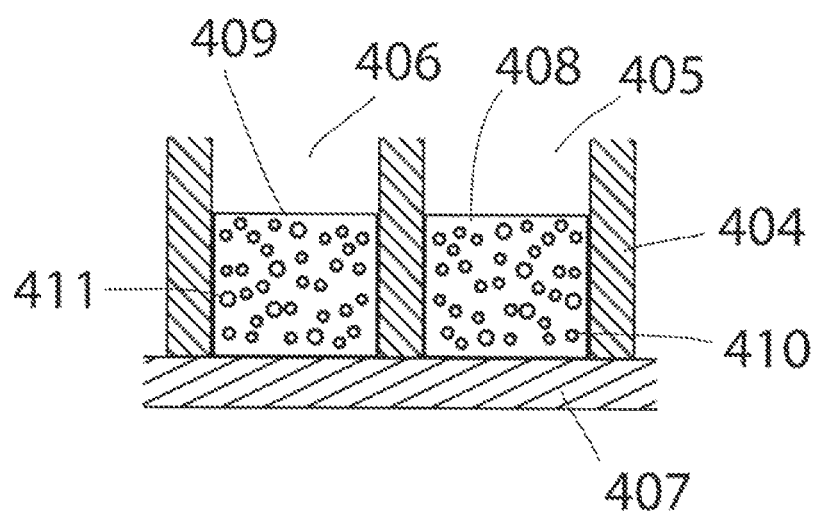
FIG. 4 a cross-section through a part of an exemplary specimen carrier comprising a positioning element and a gel.

In FIG. 4 the positioning element 404 is exemplarily fitted on a surface of a microscopy carrier 407, which can consist of plastic or glass. No liquid can penetrate between the positioning element 404 and the microscopy carrier 407. The gels 408 and 409, in which cells 410 and 411 are suspended, are introduced into the partial regions 405 and 406. Here, the gels 408 and 409 can be the same or different, similarly the cells 410 and 411 can also be the same or different. For example, both gels 408 and 409 can be produced from Collagen 1, the cells 410 can be fibroblasts and the cells 411 can be HT1080. Different cells can also be introduced into one of the gels 408 or 409.

Figure 5:
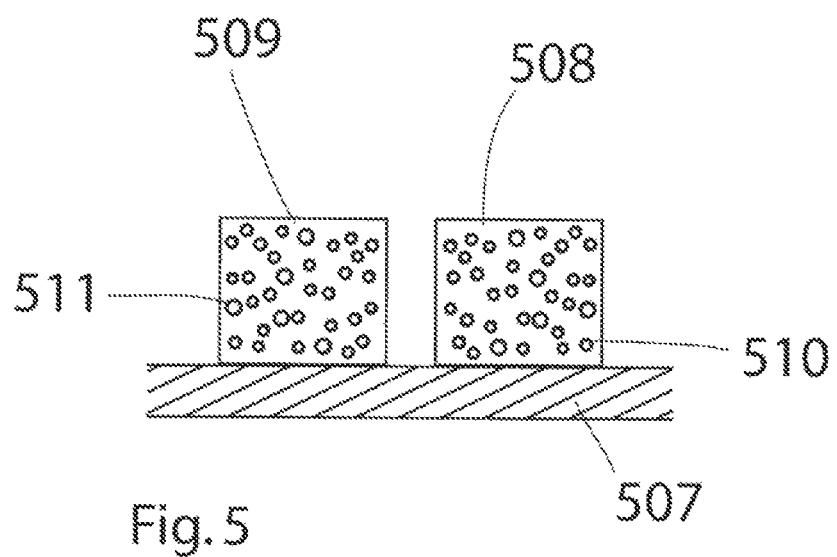
FIG. 5 a cross-section through a part of an exemplary specimen carrier and a gel arranged on it.
Figure 6:
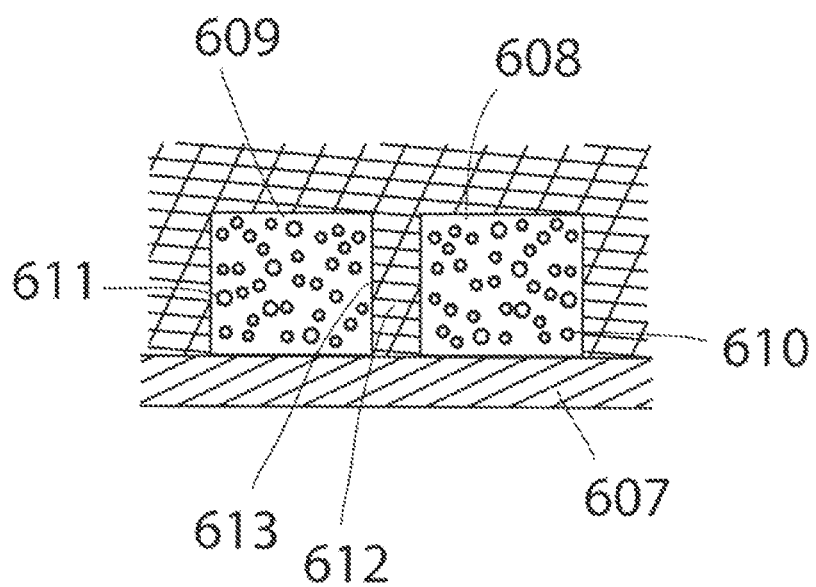
FIG. 6 a cross-section through a part of an exemplary specimen carrier and a first and second gel arranged on it.

If the gels are polymerised or gelified and the positioning element 404 is removed, as illustrated in FIG. 5, the partial regions filled with the gel 508 or 509 remain on the microscopy carrier 507. In the gel 509 the cells 511 are suspended and cells 510 in the gel 508. If, as illustrated in FIG. 6, the gap between the partial regions filled with the gel 608 or 609 is filled with a further gel 612, which can, for example, be Collagen 1 gel, cells can be observed, for example by video microscopy or with different fluorescent dyes on fibroblasts and HT1080 cells, of whether and how, for example, the tumour cells advance in the partial region of the connective tissue cells or what can be used as a metastasising model. In another experiment, for example, a gel can be used for the further gel 612 which is impenetrable to the selected cells 610 and 611, such as for example agarose. In this way the cells 610 and 611 are trapped in the partial regions on the carrier 607. If, for example, the cells 611 are drawn towards substances which are segregated from the cells 610, this can be observed in that the cells 611 accumulate on the area 613, which faces the partial region with gel 608. Cells can also be introduced into the further gel 612, in particular cells which are the same and/or different from the cells 610 and/or 611.

Figure 7:
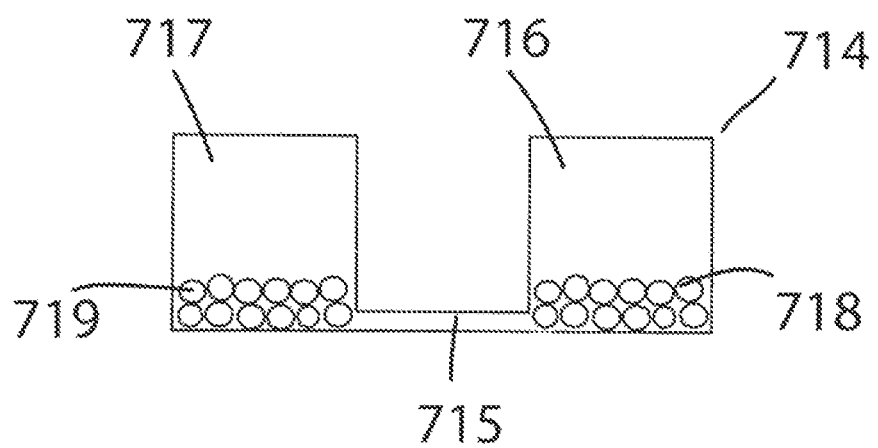
FIG. 7 a cross-section through an exemplary specimen carrier and a gel arranged in it.

In FIG. 7 an example of a specimen carrier 714 is illustrated which can be used for carrying out cell analyses in chemical gradients. An observation region or channel 715 with a small cross-section and a low height connects two reservoirs 716 and 717, which can be filled independently of one another in that they each have at least one opening (not illustrated) for filling. Gel particles 718 and 719 of expandable materials, which due to their size cannot penetrate into the channel 715, are introduced into the reservoirs 716 and 717. As a strongly swelling material, for example, a superabsorbent material such as for example polyacrylic acid can be used or also, for example, dried gelatine particles. The superabsorbent material (e.g. a superabsorbent polymer) and/or the gelatine can be introduced into and/or arranged in the specimen carrier as granulate or in the form of platelets.

Figure 8:
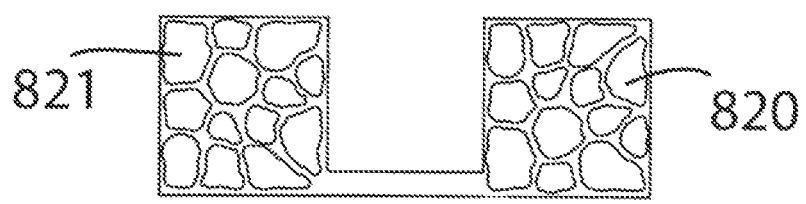
FIG. 8 a cross-section through an exemplary specimen carrier and a polymerised gel arranged in it.

Filling with gel particles can occur during the manufacture of the specimen carrier. In FIG. 8 an example of a specimen carrier is illustrated, whereby the reservoirs are filled with a liquid, so that the gel particles become swollen to the swollen gel particles 820 and 821, which completely fill the reservoirs. The quantity and/or type of gel particles can be chosen such that the volume of the completely swollen gel particles 820 and 821 is somewhat larger, e.g. by 5% to 10%, than the volumes of the reservoirs. Due to the fact that the gel cannot completely swell because of the small size of the volume, an osmotic pressure can arise in the reservoirs. This can have the effect that it is possible to fill the observation region or channel with cell suspension, which for example is suspended in a gel, through an appropriate lateral channel without cells entering the reservoirs.

Figure 9:
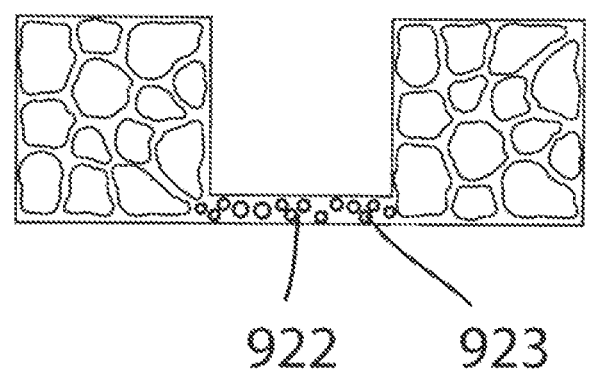
FIG. 9 a cross-section through an exemplary specimen carrier and a polymerised gel and specimens arranged in it.

FIG. 9 illustrates an example of a specimen carrier with specimens 923 suspended in a gel 922.

Figure 10:
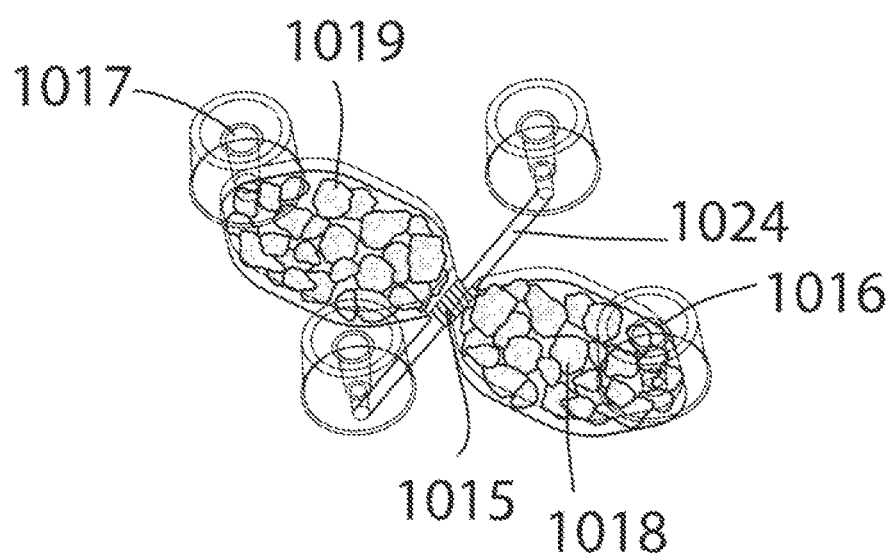
FIG. 10 an example of a specimen carrier and a polymerised gel arranged in it.

FIG. 10 shows an example of a specimen carrier comprising two reservoirs 1016 and 1017, a channel 1015, gel particles 1018 and 1019 arranged in the reservoirs 1016 and 1017 as well as a lateral channel 1024 for filling the channel 1015 with cells.

Figure 11:
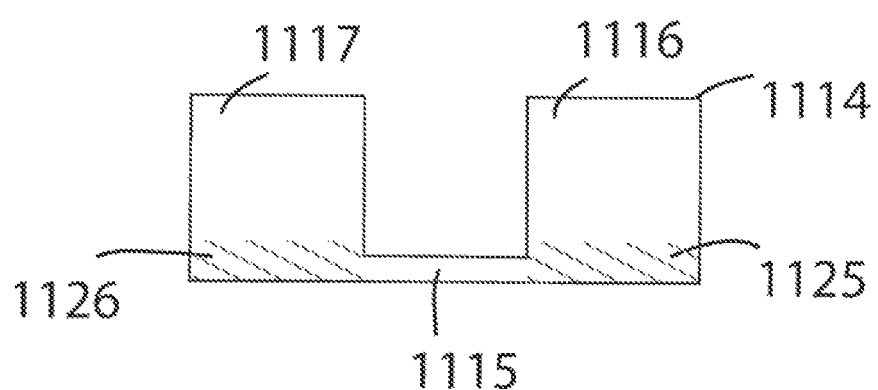
FIG. 11 a cross-section through an exemplary specimen carrier and a gel arranged in it.

FIG. 11 shows an example of a specimen carrier 1114 comprising two reservoirs 1116 and 1117 and a channel 1115, which connects the two reservoirs 1116 and 1117. Small platelets 1125 and 1126 are used as the swelling gel. Platelets of this nature can for example be stamped out of textiles in which superabsorbent materials have been incorporated. One example of this is Luquafleece® from the company Bayer. Another example of platelets 1125 and 1126 can be platelets of dried gelatine. Here, in the case of the gelatine it must be ensured that the specimen carrier, in particular the gelatine platelets arranged in it, are not heated above the melting temperature of the gelatine.

Figure 12:
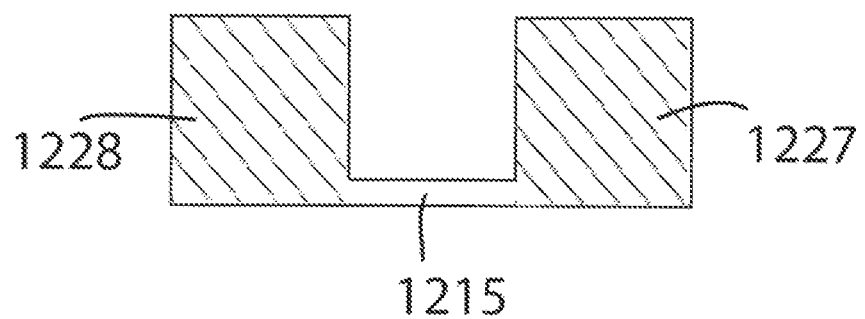
FIG. 12 a cross-section through an exemplary specimen carrier and a polymerised gel arranged in it.

In FIG. 12 an example of a specimen carrier is illustrated having swollen platelets 1227 and 1228, which completely fill the reservoirs. In particular, the volume of the reservoirs can be smaller than that of the completely swollen platelets 1227 and 1228. The observation region or channel 1215 is not swollen closed, because the polymers are dimensionally stably cross-linked.

Figure 13:
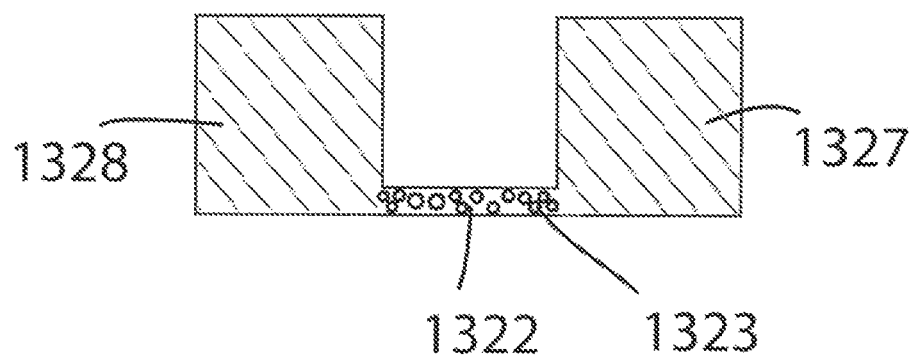
FIG. 13 a cross-section through an exemplary specimen carrier, a polymerised gel arranged in it and specimens.

In FIG. 13 an example of a specimen carrier is illustrated, whereby the observation region or channel is filled with gel 1322 with suspended cells 1323. For this, for example as shown in FIG. 10, a filling channel 1024 can be used. The reservoirs comprise swollen platelets 1327 and 1328.

Figure 14:
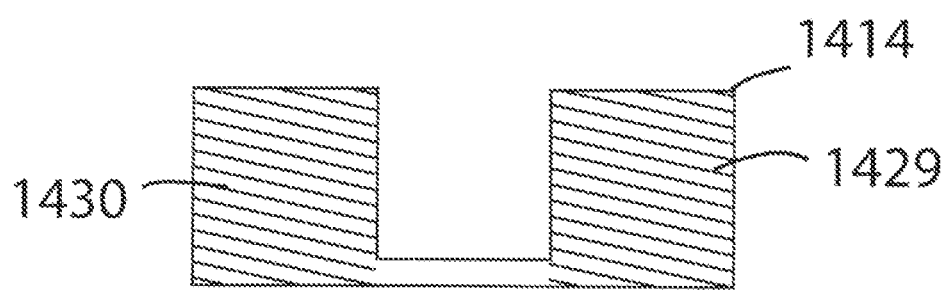
FIG. 14 a cross-section through an exemplary specimen carrier and a gel arranged in it.

In FIG. 14 the volumes of the reservoirs of an exemplary specimen carrier 1414 are filled with lyophilized gel 1429 and 1430. To achieve this, for example, Collagen 1 gel, cross-linked hyaluronic acid or gelatine can be used. Through lyophilisation the gels 1429 and 1430 can be quickly rehydrated.

Figure 15:
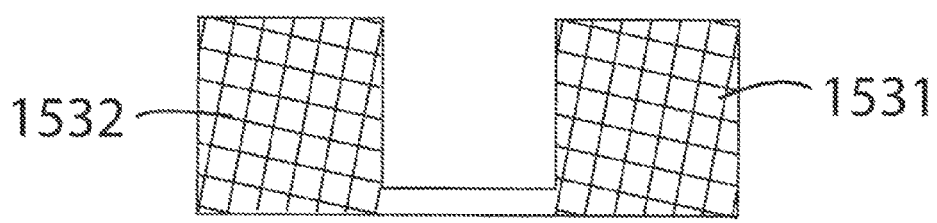
FIG. 15 a cross-section through an exemplary specimen carrier and a polymerised gel arranged in it.
Figure 16:
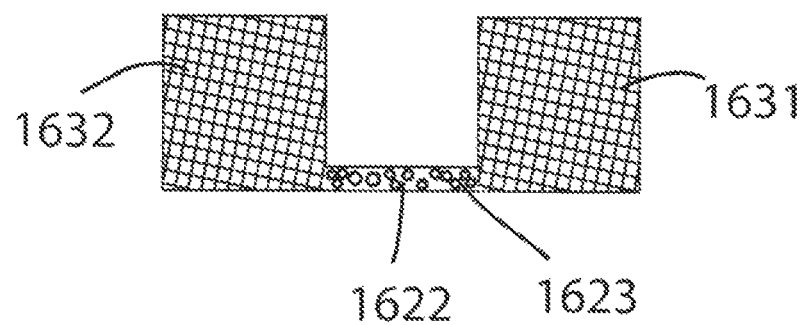
FIG. 16 a cross-section through an exemplary specimen carrier, a polymerised gel arranged in it and specimens.

The rehydrated gels 1531 and 1532 are illustrated in the reservoirs of the exemplary specimen carrier in FIG. 15. In addition to the rehydrated gels 1631 and 1632 in the reservoirs of an exemplary specimen carrier, FIG. 16 illustrates that the observation region or channel is filled with gel 1622 in which the cells 1623 are suspended.

Figure 17:
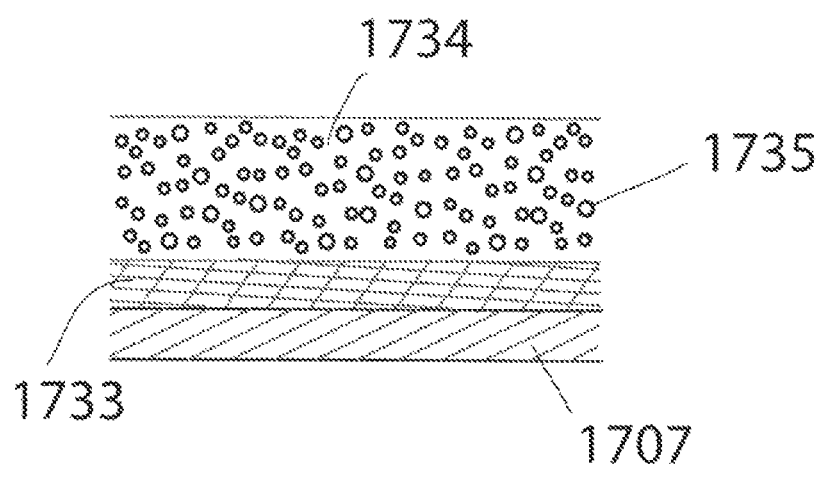
FIG. 17 part of an exemplary specimen carrier, first and second gels arranged on it and specimens arranged in the second gel.

In FIG. 17 a gel layer 1733 on a part of an exemplary specimen carrier 1707 is illustrated. Once the layer 1733 is polymerised or gelified, a further gel 1734 is applied in which the cells 1735 are suspended. In this way the cells 1735 can be prevented from coming into contact with a surface of the specimen carrier 1707 and adhering to the surface due to durotaxis.

Figure 18:
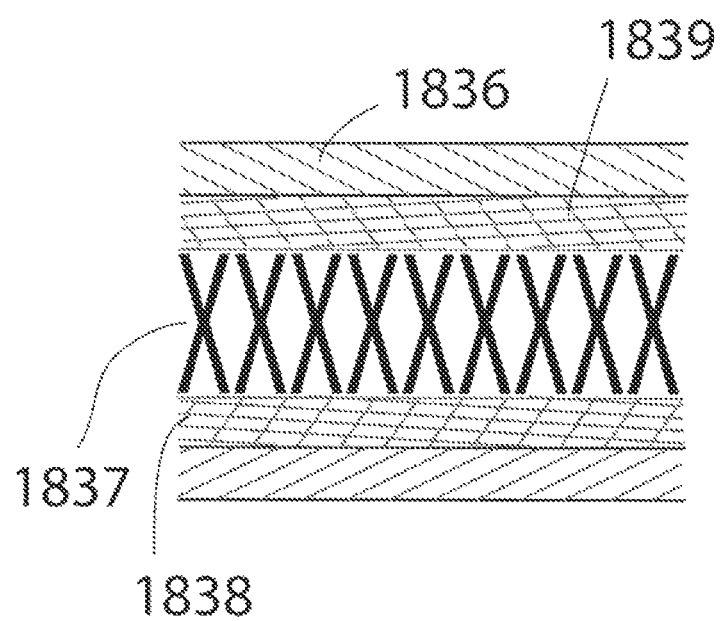
FIG. 18 part of an exemplary specimen carrier comprising a positioning element.

In FIG. 18 part of an exemplary specimen carrier is illustrated which is delimited by a lower part and an upper part 1836. A positioning element in the form of a slide 1837 is arranged between the upper and lower parts such that defined volumes 1838 and 1839 remain free in each case between the slide 1837 and the lower and upper sides. These volumes are filled with gel and the gel polymerised out or gelified. Then the slide 1837 is removed, by means of which a gel-free volume or a gel-free partial region remains.

Figure 19:
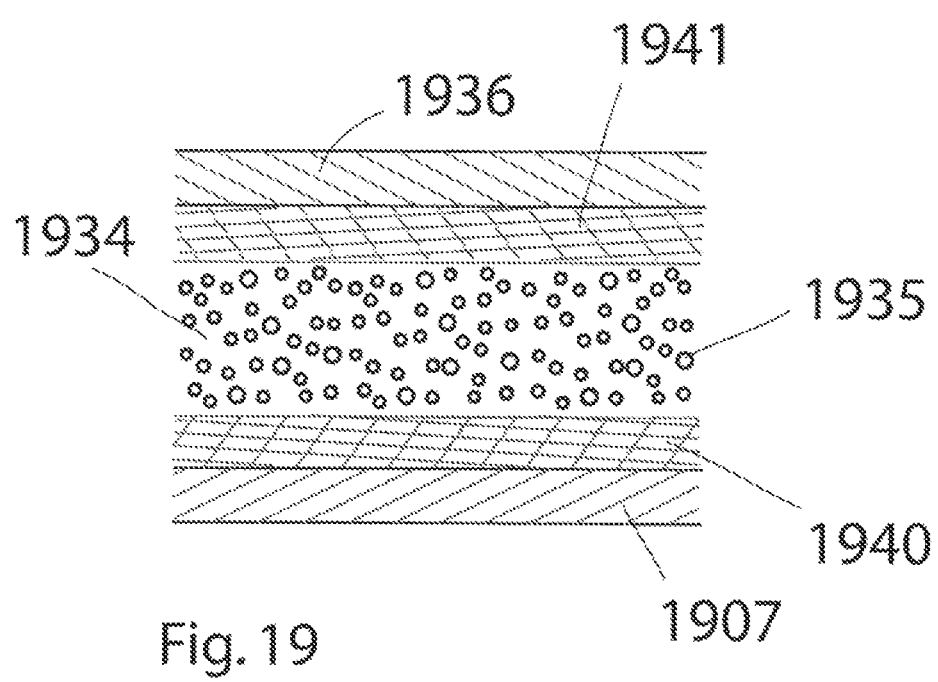
FIG. 19 part of an exemplary specimen carrier, first and second gels arranged on it and specimens arranged in the second gel.

As shown in FIG. 19, this can then be filled with a further gel 1934 in which the cells 1935 are suspended. In this way the cells 1935 can be cultured in a small volume without them noticing a hard surface of the specimen carrier 1907, for example also of the upper part 1936. For this purpose preferably gels through which the cells cannot penetrate can be used as the gels 1940 and 1941.

Figure 20:
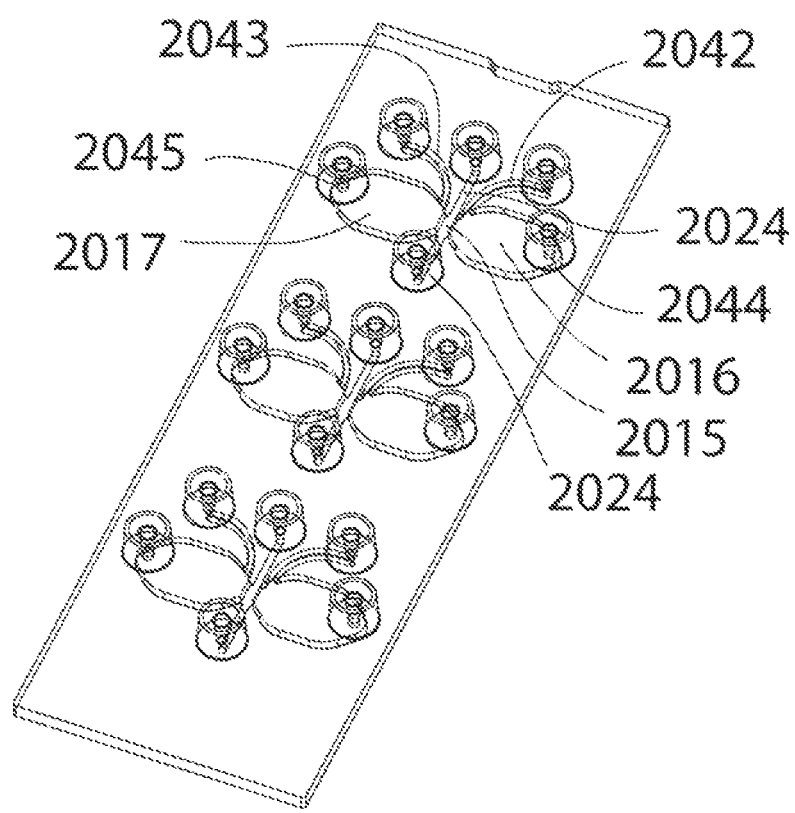
FIG. 20 an example of a specimen carrier comprising two reservoirs and a channel.

In FIG. 20 an exemplary specimen carrier is illustrated with the aid of which chemotaxis in three dimensions can be examined. To do this, with the aid of a lateral channel 2024 an observation region or channel 2015 is first filled with a gel, in which cells are suspended, and the gel is allowed to polymerise or gelify there. In this case the channel can be dimensioned such that the gel and the specimen are held in the channel by capillary forces, i.e. they are not emitted from the channel. Then a reservoir 2016 is filled via a channel 2042, whereby the reservoir is vented via an opening 2044. A second reservoir 2017 is filled appropriately via a filling channel 2043 and an opening 2045 provides venting. It is important for the establishment of a stable diffusive gradient that all connections are hermetically sealed by appropriate plugs, as described for example in EP 1 741 487.

Figure 21:
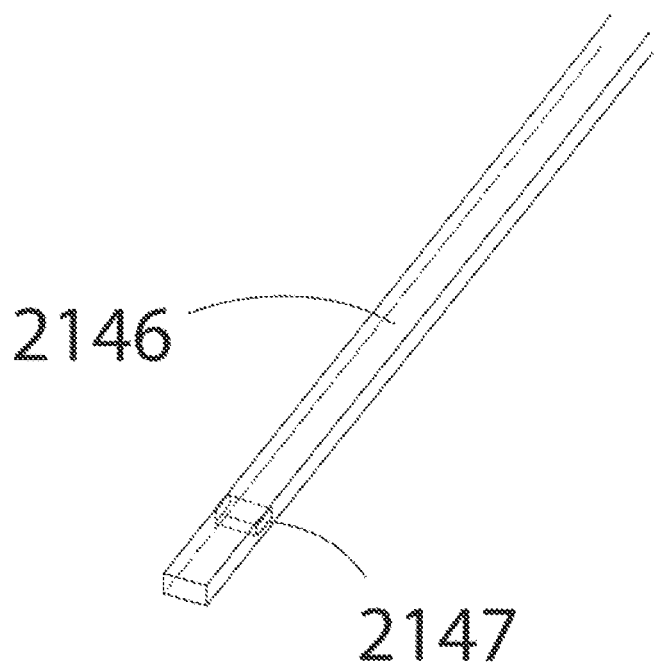
FIG. 21 an example of a positioning element.

In FIG. 21 an example of a positioning element in the form of a slide 2146 is illustrated, which can be used to push or to position a volume 2147, which is left blank in the slide, to a certain location in a specimen carrier. The volume 2147 can in particular be filled with a gel containing particles or cells, for example before the slide is partially or completely introduced into a channel provided specifically for it in the specimen carrier, to suitably position the gel. The slide 2146 can be injection moulded in one piece or manufactured in that a film is applied to a small rectangular rod which has a recess of the size of the volume 2147.

Figure 22:
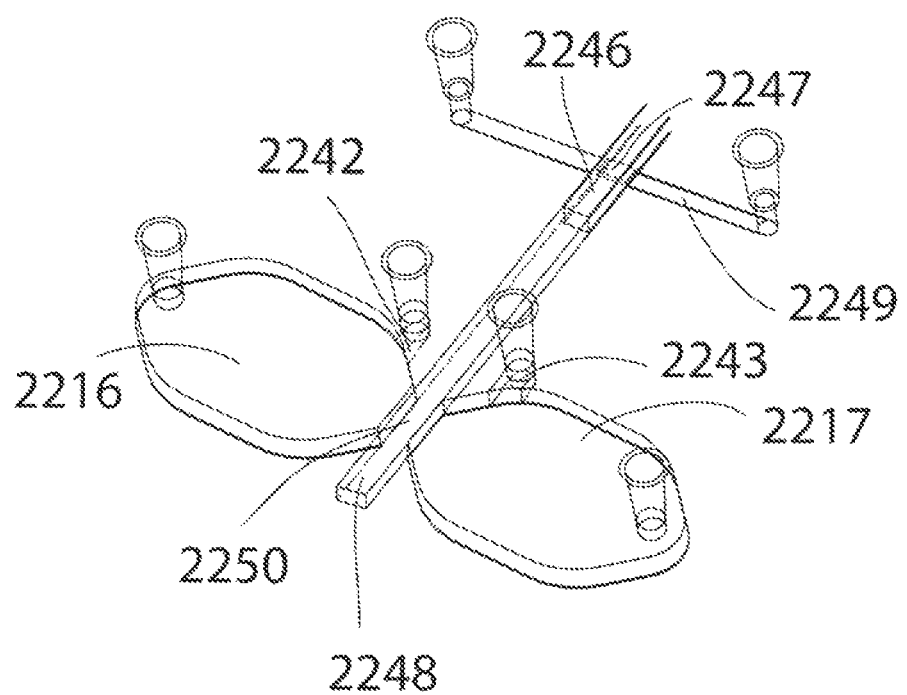
FIG. 22 an example of a specimen carrier and a positioning element.

In FIG. 22 an example is shown of how a slide 2246 of this nature can be introduced e.g. into a chemotaxis device. In the position illustrated the slide 2246, in particular the reserved volume 2247, can be filled with gel containing cells, for example through a lateral channel 2249. With the aid of the slide 2246 and depending on the desired filling protocol, the region between the reservoirs 2216 and 2217 can be closed off in that the slide in the channel 2248 is pushed further forward to fill the reservoirs 2216 and 2217 independently of one another, for example with the aid of the connections 2242 and 2243. The reservoirs 2216 and 2217 can alternatively be filled with gel or with a Newtonian fluid. The gel, with which the volume 2247 is filled, can be retrospectively introduced in a defined manner into the observation region 2250 between the reservoirs 2216 and 2217.

Figure 23:
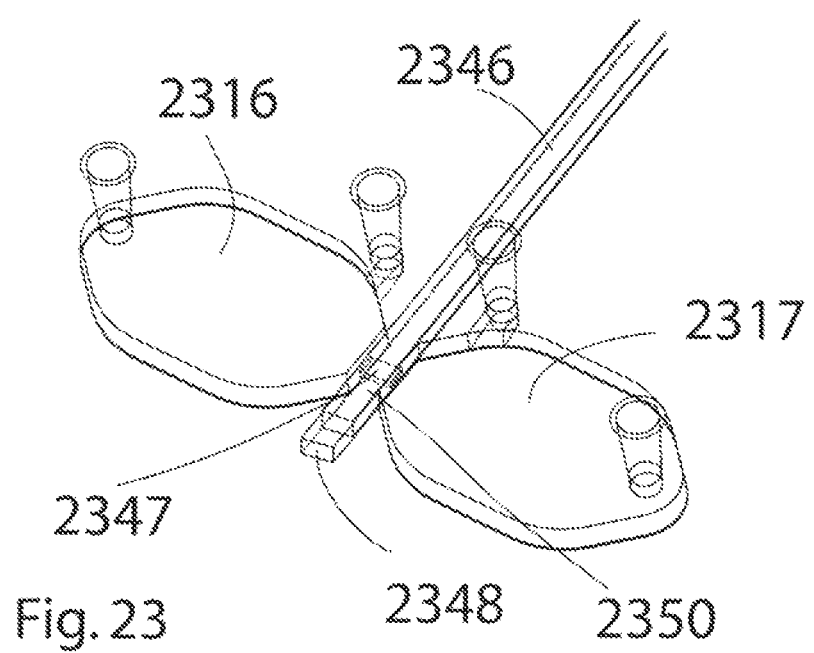
FIG. 23 an example of a specimen carrier with introduced positioning element.

In FIG. 23 an example of a positioning element in the form of a slide 2346 is illustrated, which has been introduced into a specimen carrier. In particular the slide 2346 is arranged in the channel 2348 such that the gel with which the volume 2347 is filled is arranged in the observation region 2350 between the reservoirs 2316 and 2317. The channel 2348 can be sealed with respect to the slide 2346 after the pushing process using viscous silicone oil or silicone which can be polymerised, such as for example PDMS (polydimethylsiloxane). As an alternative, sealing can also be carried out, for example, with the aid of O-ring seals between the channel 2348 and slide 2346.

Figure 24:
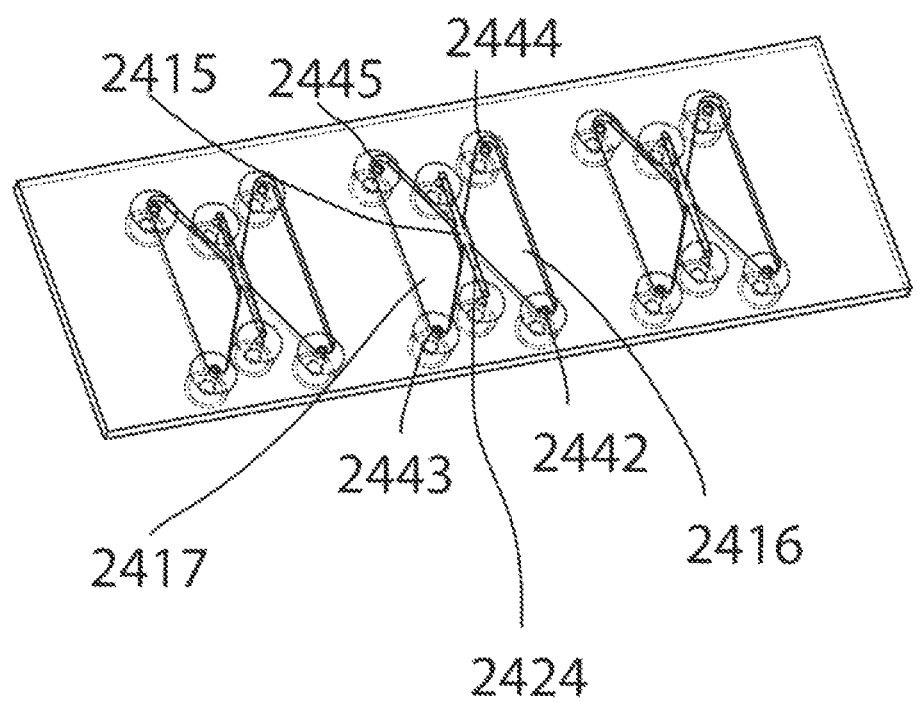
FIG. 24 an example of a specimen carrier.

FIG. 24 illustrates a further example of a specimen carrier. In particular this specimen carrier represents a further exemplary structure with which it is possible to fill a defined space with gel. To do this, the observation region 2415 is filled via the channel 2424 with, for example Collagen 1 gel, in which cells are suspended, and it is allowed to polymerise. Here, the observation region 2415 can be dimensioned such that the introduced gel is held in the observation region 2415 by capillary forces, i.e. it does not encroach into the reservoirs 2416 and 2417. Then the reservoir 2416 is filled via the connections 2442 and 2444 and the reservoir 2417 via the connections 2443 and 2445 with Newtonian fluids or gels. If the reservoirs 2416 and 2417 are then closed off hermetically, for example with suitable conical plugs, a gradient, in which the migration of the cells can be observed, becomes established in the region 2415 due to diffusion.

It is self-evident that the features mentioned in the previously described embodiments are not restricted to these particular combinations and are possible in any other combinations. In particular different specimen carriers can be combined with different process steps in a different sequence.

The invention claimed is:

1. A method of positioning an organic, biological and/or medical specimen in a desired partial region of a specimen carrier, comprising the steps:
   arrangement of a non-polymerised or non-gelified gel in a partial region of the specimen carrier;
   polymerisation or gelification of the gel, by means of which a polymerised gel is obtained, wherein the polymerised gel borders at least partially the desired partial region; and
   introduction of the specimen into the specimen carrier, wherein the specimen comprises a plurality of cells, wherein the polymerisation or gelification of the gel occurs after the arrangement of the gel.

2. Method according to claim 1, wherein the polymerised gel is arranged and/or formed such that dissemination of the specimen out of the desired partial region within the specimen carrier is prevented.

3. Method according to claim 2, wherein the polymerised gel is arranged and/or formed such that dissemination of the specimen out of the desired partial region within the specimen carrier is prevented during the introduction of the specimen into the specimen carrier.

4. Method according to claim 2, wherein the polymerised gel is arranged and/or formed such that dissemination of the specimen out of the desired partial region within the specimen carrier in the horizontal direction is prevented.

5. Method according to claim 1, wherein the introduction of the specimen occurs before, during and/or after the polymerisation or gelification of the gel.

6. Method according to claim 1, wherein the introduction of the specimen comprises an introduction of the specimen into the gel.

7. Method according to claim 6, wherein the introduction of the specimen into the gel occurs before the arrangement of the gel.

8. Method according to claim 1, wherein in the desired partial region no polymerised gel is arranged or wherein polymerised gel is arranged in the desired partial region.

9. Method according to claim 8, wherein in the desired partial region no polymerised gel is arranged or wherein polymerised gel is arranged in the whole desired partial region.

10. Method according to claim 1, comprising an introduction of a further gel into the specimen carrier.

11. Method according to claim 10, wherein the specimen with the further gel is introduced into the specimen carrier.

12. Method according to claim 11, wherein the specimen with the further gel is introduced into the specimen carrier in the form of a suspension in the further gel.

13. Method according to claim 10, comprising an introduction of a further gel into the desired partial region of the specimen carrier.

14. Method according to claim 1, wherein the arrangement of the gel comprises an arrangement of a positioning element in a partial region of the specimen carrier, and wherein the positioning element prevents a dissemination of the gel into the desired partial region or out of the desired partial region.

15. Method according to claim 14, wherein the positioning element is removed during or after the polymerisation or gelification of the gel.

16. Method according to claim 14, wherein the arrangement of the gel comprises an arrangement of a positioning element in a partial region of the specimen carrier comprising the desired partial region.

17. Method according to claim 1, wherein the desired partial region is fully delimited by the polymerised gel or by the polymerised gel and the specimen carrier.

18. Method according to claim 1, wherein the specimen carrier comprises a cavity, and wherein the desired partial region is arranged in the cavity.

19. Method according to claim 18, wherein the partial region of the specimen carrier in which the gel is arranged, corresponds to a partial region of the cavity, and wherein the volume of the partial region is smaller than the volume of the polymerised or gelified gel.

20. Method according to claim 19, wherein the volume of the partial region is 5%-10% smaller than the volume of the polymerised or gelified gel.

21. Method according to claim 1, wherein the polymerised gel horizontally borders at least partially the desired partial region.

22. Method according to claim 1, wherein the specimen is introduced into the specimen carrier into the desired partial region of the specimen carrier.

23. Method of preparing a specimen carrier, comprising:
introducing a non-polymerised or non-gelified gel into the specimen carrier; and
polymerising or gelifying the gel in the specimen carrier, thereby preventing adhesion of an organic, biological and/or medical specimen on a surface of the specimen carrier, wherein the specimen comprises a plurality of cells.

* * * * *